US00PP21702P2

(12) United States Plant Patent
Dümmen

(10) Patent No.: US PP21,702 P2
(45) Date of Patent: Feb. 8, 2011

(54) **NEW GUINEA *IMPATIENS* PLANT NAMED 'DUESWEETBLUST'**

(50) Latin Name: *Impatiens hawkeri*
Varietal Denomination: Duesweetblust

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/587,124

(22) Filed: Oct. 1, 2009

(51) Int. Cl.
*A01H 5/00* (2006.01)

(52) U.S. Cl. ..... Plt./318.6

(58) Field of Classification Search ..... Plt./318.1, Plt./318.6
See application file for complete search history.

(56) References Cited

PUBLICATIONS

UPOV-ROM GTITM, Plant Variety Database, 2010/04, GTI Jouve Retrieval Software, citation for 'Duesweetblust'.*

* cited by examiner

*Primary Examiner*—Susan B McCormick Ewoldt
(74) *Attorney, Agent, or Firm*—C. A. Whealy

(57) ABSTRACT

A new and distinct cultivar of *Impatiens* plant named 'Duesweetblust', characterized by its compact, upright and outwardly spreading growth habit; mounded plant habit; freely branching habit; moderately vigorous growth habit; dark green-colored leaves; freely and early flowering habit; large light and dark red purple bi-colored flowers; and good garden performance.

1 Drawing Sheet

Botanical designation: *Impatiens hawkeri.*
Cultivar denomination: 'DUESWEETBLUST'.

BACKGROUND OF THE INVENTION

The present invention relates to a new and distinct cultivar of New Guinea Impatiens plant, botanically known as *Impatiens hawkeri* and hereinafter referred to by the name 'Duesweetblust'.

The new *Impatiens* plant is a product of a planned breeding program conducted by the Inventor in Rheinberg, Germany. The objective of the breeding program is to create new compact New Guinea Impatiens plants with large and attractive flowers.

The new *Impatiens* plant originated from a cross-pollination made by the Inventor in July, 2003 in Rheinberg, Germany of a proprietary selection of *Impatiens hawkeri* identified as code number F-07-21, not patented, as the female, or seed, parent with a proprietary selection of *Impatiens hawkeri* identified as code number N96-0575-053, not patented, as the male, or pollen, parent. The new *Impatiens* plant was discovered and selected by the Inventor as a single flowering plant from within the progeny of the stated cross-pollination in a controlled greenhouse environment in Rheinberg, Germany in May, 2006.

Asexual reproduction of the new *Impatiens* plant by terminal cuttings in a controlled greenhouse environment in Rheinberg, Germany since May, 2006, has shown that the unique features of this new *Impatiens* plant are stable and reproduced true to type in successive generations.

SUMMARY OF THE INVENTION

Plants of the new *Impatiens* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duesweetblust'. These characteristics in combination distinguish 'Duesweetblust' as a new and distinct cultivar of *Impatiens:*

1. Compact, upright and outwardly spreading growth habit; mounded plant habit.
2. Freely branching habit.
3. Moderately vigorous growth habit.
4. Dark green-colored leaves.
5. Freely and early flowering habit.
6. Large light and dark red purple bi-colored flowers.
7. Good garden performance.

Plants of the new *Impatiens* can be compared to plants of the female parent selection. Plants of the new *Impatiens* differ from plants of the female parent selection in the following characteristics:

1. Plants of the new *Impatiens* are more compact than plants of the female parent selection.
2. Plants of the new *Impatiens* and the female parent selection differ in flower color.

Plants of the new *Impatiens* can be compared to plants of the male parent selection. Plants of the new *Impatiens* differ from plants of the male parent selection primarily in flower color.

Plants of the new *Impatiens* can be compared to plants of New Guinea Impatiens 'Kimpgua', disclosed in U.S. Plant Pat. No. 10,429. In side-by-side comparisons conducted in Rheinberg, Germany, plants of the new *Impatiens* differed from plants of 'Kimpgua' in the following characteristics:

1. Plants of the new *Impatiens* were more compact than plants of 'Kimpgua'.

2. Plants of the new *Impatiens* had shorter internodes than plants of 'Kimpgua'.
3. Plants of the new *Impatiens* and 'Kimpgua' differed in flower color.

BRIEF DESCRIPTION OF THE PHOTOGRAPH

The accompanying colored photograph illustrates the overall appearance of the new *Impatiens* plant, showing the colors as true as it is reasonably possible to obtain in colored reproductions of this type. Colors in the photograph may differ slightly from the color values cited in the detailed botanical description which accurately describe the colors of the new *Impatiens* plant. The photograph comprises a side perspective view of a typical flowering plant of 'Duesweetblust' grown in a container.

DETAILED BOTANICAL DESCRIPTION

The aforementioned photograph and following observations, measurements and values describe plants grown in Rheinberg, Germany, in containers and under commercial practice during the summer in a glass-covered greenhouse with day and night temperatures averaging 18° C. and light levels averaging 4,500 lux. Plants were pinched three weeks after planting and were 16 weeks old when the photograph and description were taken. In the following description, color references are made to The Royal Horticultural Society Colour Chart, 2001 Edition, except where general terms of ordinary dictionary significance are used.

Botanical classification: *Impatiens hawkeri* 'Duesweetblust'.

Parentage:

*Female, or seed, parent.*—Proprietary selection of *Impatiens hawkeri* identified as code number F-07-21, not patented.

*Male, or pollen, parent.*—Proprietary selection of *Impatiens hawkeri* identified as code number N96-0575-053, not patented.

Propagation:

*Type.*—By terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching; dense.

Plant description:

*Plant and growth habit.*—Compact, upright to outwardly spreading growth habit; mounded plant habit; freely branching habit with about seven lateral branches; pinching is typically not required; moderately vigorous growth habit.

*Plant height.*—About 14 cm.

*Plant diameter.*—About 17 cm.

Lateral branch description:

*Length.*—About 10 cm.

*Diameter.*—About 7 mm.

*Internode length.*—About 2.3 cm.

*Strength.*—Strong.

*Aspect.*—Initially upright to outwardly spreading.

*Texture.*—Smooth, glabrous.

*Color.*—Close to 144A.

Foliage description:

*Arrangement.*—Opposite or in whorls; simple.

*Length.*—About 9.2 cm.

*Width.*—About 3 cm.

*Shape.*—Ovate.

*Apex.*—Apiculate.

*Base.*—Obtuse.

*Margin.*—Serrulate with ciliation.

*Texture, upper and lower surfaces.*—Smooth, glabrous; leathery.

*Venation pattern.*—Pinnate; arcuate.

*Color.*—Developing and fully expanded leaves, upper surface: Close to 139A; venation, close to 59A. Developing and fully expanded leaves, lower surface: Close to 59A; venation, close to 59A.

*Petiole length.*—About 1.4 cm.

*Petiole diameter.*—About 3 mm.

*Petiole texture, upper and lower surfaces.*—Smooth, glabrous.

*Petiole color, upper and lower surfaces.*—Close to 60A.

Flower description:

*Flower type and flowering habit.*—Single rounded and flat axillary flowers; freely flowering habit; typically about seven open flowers and flower buds per lateral branch; flowers positioned above the foliar plane and typically face upright or outward.

*Flower longevity.*—Flowers typically last about five to six days under greenhouse conditions; petals self-cleaning, gynoecium persistent.

*Fragrance.*—Flowers are not fragrant.

*Natural flowering season.*—Year-round under greenhouse conditions; in the garden, flowering from spring until fall in Germany; early flowering habit, plants typically begin flowering about eight weeks after planting.

*Flower size.*—Length: About 6 cm. Diameter: About 6 cm. Depth: About 2.3 cm.

*Flower buds.*—Length: About 1 cm. Diameter: About 8 mm. Shape: Ovate. Color: Close to 57A to 57B.

*Petals.*—Quantity/arrangement: Five per flower in a single whorl. Length: About 3 cm. Width: About 3.7 cm. Shape: Obcordate. Apex: Emarginate; rounded. Base: Acute. Margin: Entire. Texture, upper and lower surfaces: Smooth, glabrous; satiny. Color: When opening, upper surface: Ground color, close to 74B; center, central stripes and banner blotch, close to 66A. When opening, lower surface: Ground color, close to 74B; center and central stripes, close to 46A to 46B. Fully opened, upper surface: Ground color, close to 74B to 74C; center, central stripes and banner blotch, close to 66A; with development, ground color becoming closer to 74D and center, central stripes and banner blotch color becoming closer to 53A. Fully opened, lower surface: Ground color, close to 66C; center and central stripes, close to 45B.

*Sepals.*—Quantity/arrangement: Three; one modified into an elongated spur. Length: About 1 cm. Width: About 5 mm. Shape: Oval. Apex: Acute. Base: Obtuse. Margin: Entire. Texture, upper and lower surfaces: Smooth, glabrous. Color, upper and lower surfaces: Close to 147A. Spur length: About 4.8 cm. Spur diameter: At flower, about 3 mm; at apex, less than 1 mm. Spur texture: Smooth, glabrous. Spur color: Close to 149A tinted with close to 58D.

*Peduncles.*—Length: About 4.2 cm. Diameter: About 2 mm. Angle: Upright to outward. Strength: Moderately strong; flexible. Texture: Smooth, glabrous. Color: Close to 144A.

*Reproductive organs.*—Stamens: Quantity: Five fused at anthers; filaments free. Anther length: About 5 mm. Anther shape: Oval. Anther color: Close to 155B tinted with close to 61C. Pollen amount: Abundant. Pollen color: Close to 11D. Pistils: Quantity per flower: One. Pistil length: About 5 mm. Stigma shape: Crested. Stigma color: Close to 61A. Style color: Close to 61A. Ovary color: Close to 187A.

*Seed/fruit.*—Seed and fruit production have not been observed.

Disease/pest resistance: Plants of the new *Impatiens* have not been observed to be resistant to pathogens and pests common to New Guinea Impatiens.

Garden performance: Plants of the new *Impatiens* have been observed to have good garden performance and tolerate temperatures ranging from about 5° C. to about 40° C.

It is claimed:

1. A new and distinct *Impatiens* plant named 'Duesweetblust' as illustrated and described.

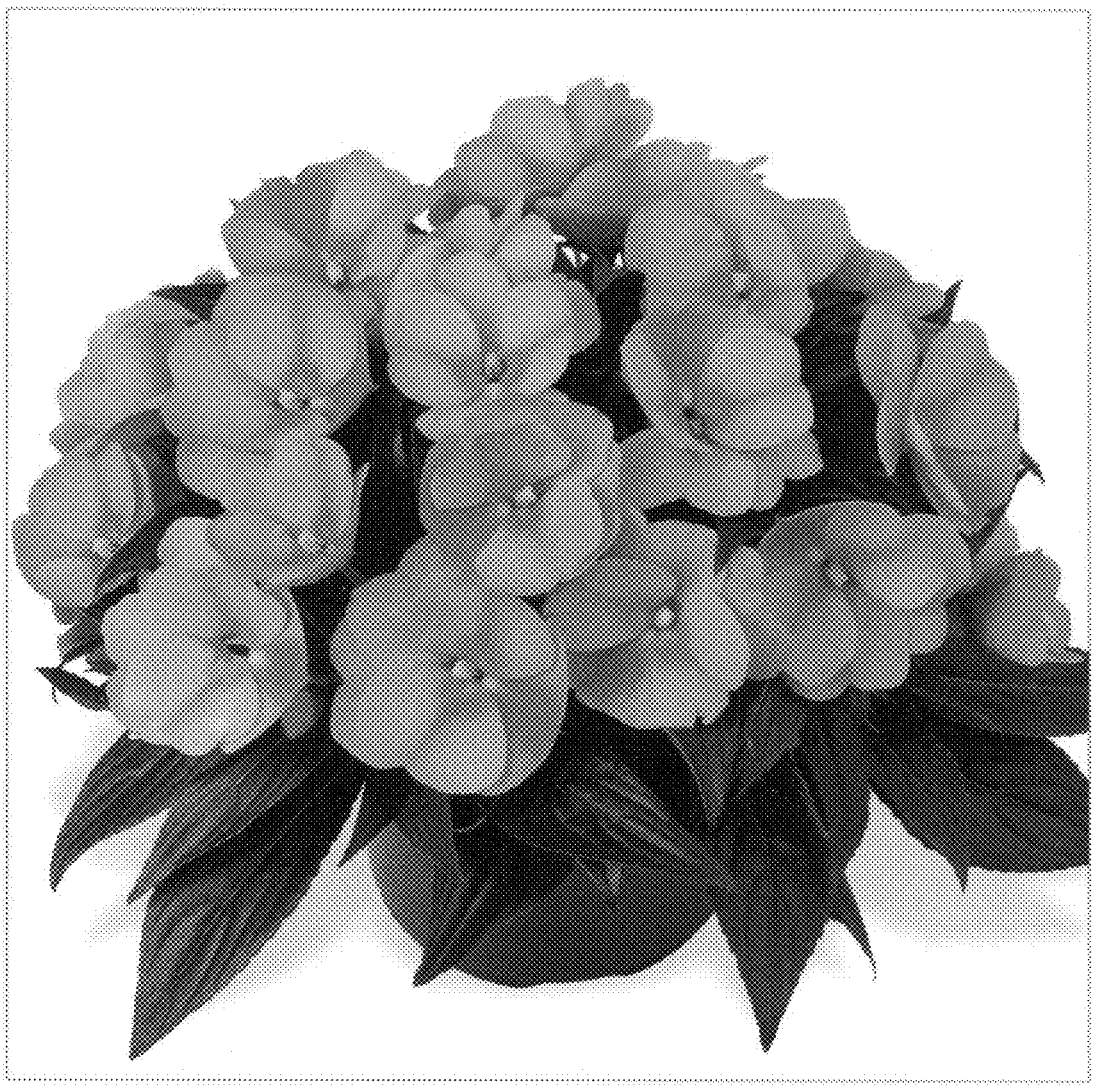

* * * * *